United States Patent
Yun-Choi et al.

(10) Patent No.: US 6,562,837 B1
(45) Date of Patent: May 13, 2003

(54) USE OF TETRAHYDROISOQUINOLINE COMPOUNDS FOR THE TREATMENT OF SEPTICEMIA

(75) Inventors: Hye Sook Yun-Choi, #11-205 Shindonga Apt., 241-21 Seobinggo-dong, Yongsan-ku, Seoul 140-751 (KR); Ki-Churl Chang, #106-102 Hyundai Apt., Shinan-dong, Jinjoo-si, Kyungsangnam-do 660-100 (KR); Duck-Hyung Lee, #6-802 JinHeung Apt., Anyang 3-dong, Manan-ku, Anyang-si, Kyunggi-do 430-013 (KR); Jae-Chun Ryu, Seoul (KR)

(73) Assignees: Korea Institute of Science & Technology, Seoul (KR); Hye Sook Yun-Choi, Seoul (KR); Ki-Churl Chang, Kyungsangnam-do (KR); Duck-Hyung Lee, Kyunggi-do (KR)

( * ) Notice: Subject to any disclaimer, the term of this patent is extended or adjusted under 35 U.S.C. 154(b) by 0 days.

(21) Appl. No.: 09/806,389
(22) PCT Filed: Jan. 21, 1999
(86) PCT No.: PCT/KR99/00631
§ 371 (c)(1), (2), (4) Date: Mar. 29, 2001
(87) PCT Pub. No.: WO00/23078
PCT Pub. Date: Apr. 27, 2000

(30) Foreign Application Priority Data

Oct. 21, 1998 (KR) .............................. 98/44128
Sep. 22, 1999 (KR) .............................. 99/41208

(51) Int. Cl.⁷ .................................... A61K 31/47
(52) U.S. Cl. .................................... 514/307
(58) Field of Search ........................ 514/307

(56) References Cited

FOREIGN PATENT DOCUMENTS

KR          96-22471    *    7/1996

OTHER PUBLICATIONS

"Cardiovascular effect of a naphthylmethyl substituted tetrahydroisoquinoline, YS 49, in rat and rabbit", Lee et al., Life Sciences, 1994 55 921), PL 415–20, abstract.*

An article entitled Prevention of the Expression of Inducible Nitric Oxide Synthase by a Novel . . . , By Kang et al., published by British Journal of Pharmacology (1999) vol. 128, pp. 357–364.

An article entitled Inhibition of Activation of Nuclear Factor KB is Responsible . . . , by Kang et al., published by the Journal of Pharmacology and Experimental Therapeutics (1999) vol. 291, pp. 314–320.

An article entitled Comparison of Inodilator Effect of Higenamine, YS49, YS51 . . . , By Chong et al., published by Korean J. Physical Pharmacol, vol. 2, Jun. 1998, pp. 323–330.

An article entitled Different Pharmacological Characteristics of Structurally Similar Benzylisoquinoline Analogs . . . , by Chang et al., published by Department of Pharmacology and Cardiovascular Research Institute, Jan. 22, 1993, pp. 327–334.

\* cited by examiner

Primary Examiner—Zohreh Fay
Assistant Examiner—Brian Kwon
(74) Attorney, Agent, or Firm—Bachman & LaPointe, P.C.

(57) ABSTRACT

Disclosed are pharmaceutical compositions for the treatment and prophylaxis of heart failure, thrombosis, iNOS-induced tissue injury, septicemia, and disseminated intravascular coagulation. The compositions comprise, as a pharmacologically active ingredient, the compounds represented by the following chemical formulas 1 and 2, each of them showing heart stimulating activity, hypotensive activity, inhibitory activity against platelet aggregation, and suppressive activity against iNOS expression in combination and at once.

Chemical Formula 1

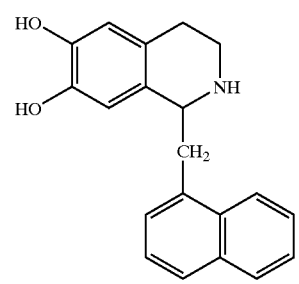

Chemical Formula 2

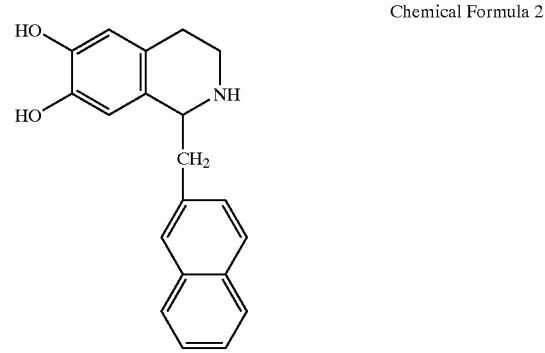

4 Claims, 10 Drawing Sheets

USE OF TETRAHYDROISOQUINOLINE COMPOUNDS FOR THE TREATMENT OF SEPTICEMIA

This application is a 371 of PCT/KR99/00631 Jan. 21, 1999.

TECHNICAL FIELD

The present invention relates, in general, to novel pharmaceutical uses of tetrahydroisoquinoline compounds represented by the following chemical formula 1 and 2. More particularly, the compounds of the present invention can be used to therapeutically effective ingredients in pharmaceutical compositions for treating heart failure, thrombosis, septicemia, disseminated intravascular coagulation (hereinafter referred to as "DIC") and/or tissue injuries mediated by nitric oxide (NO), which is clearly driven from enhancement of inducible NO synthase (hereinafter referred to as "iNOS") induction:

Chemical Formula 1

Chemical Formula 2

Tetrahydroisoqunoline (hereinafter referred to as "THI") compounds are in the ring closing state of N-alkylphenylethylamines. Particularly, the chemical structures of 6,7-dihydroxytetrahydroisoquinolines possess a common backbone of catecholamine. That is, they contain, in their structures, 3,4-dihydroxyphenylethylamine, which is the backbone of catecholamine of which epinephrine, norepinephrine and dopamine are representative. Thus, many THI compounds show affinity for adrenergic receptors. In addition, it is reported that, depending on substituents' kinds and their binding positions, THI compounds act on α- and/or β-receptors and exert agonistic and/or antagonistic effects, thereby exhibiting various pharmacological activities.

Particularly, THI compounds which have an hydroxy (OH—), methoxy(OCH$_3$—), or halogen-substituted benzyl group on the carbon at the 1-position, are reported to show potent activities, such as bronchodilation, inhibitory activity against platelet aggregation, calcium channel blocking action, etc (King, V. F. et al., *J. Biol. Chem.*, 263, 2238–2244, 1988; Triggle, D. J. et al., *Med. Res. Rev.*, 9, 123–180, 1989; Lacorix, P. et al., *Eur. J. Pharmacol.*, 192, 317–327, 1991; Chang, K. C. et al., *Life. Sci.*, 51, 64–74, 1992; Chang, K. C. et al., *Eur. J. Pharmacol.*, 238, 51–60, 1993).

Recently, bisbenzyl-tetrahydroisoquionoline compounds, such as tetrandrine, isotetrandrine and chondrocurine, have been disclosed to have a potent inhibitory activity against the mass production of NO induced by the endotoxin lipopolysaccharide (hereinafter referred to as "LPS") (Kondo, Y. et al., *Biochem. Pharmacol.*, 46, 1861–1863, 1993).

Higenamine, a THI compound containing a 4-hydroxybenzyl group at the position-1 and a hydroxy group at each of the positions-6 and -7, is very similar in structure to dobutamine which is clinically used as a cardiotonic agent. Higenamine is found to increase myocardial contractile force and heart rate and inhibit platelet aggregation in vitro experiments using isolated hearts and to show the increasing of cardiac output, hypotensive action, and anti-platelet aggregation in vivo experiments using rats or rabbits. In experiments using peritoneal macrophages of mice and thoracic aorta preparations from rats, higenamine was also reported to inhibit expression of iNOS and NO production by LPS, which accounted for restoration of the depressed vascular reactivity and lower the mortality due to endotoxin (Y. J. Kang et al., *J.Pharmacol. Exp. Ther*. 291, 314–320, 1999). Further, in an arthritis model, anti-inflammatory and analgesic activity were observed from higenamine (Park, C. W. et al., *Arch. Int. Pharmacodyn.*, 267, 279–288, 1984; Chang, K. C. et al., *Can. J. Physiol. Pharmacol.*, 72, 327–334, 1994; Yun-Choi, H. S. et al., *Yakhak Hoeju*, 38, 191–196, 1994; Kang, Y. J. et al., *Kor. J. Physiol. Phamacol.*, 1, 297–302, 1997; Shin, K. H. et al., *Natural Products Sciences*, 2, 24–28, 1996) However, higenamine is disadvantageous in that it shows a drug effect only for a short period of time and the aforementioned pharmacological actions are insufficient.

As a result of the research on the development of higenamine derivatives having superior pharmacological effects, the present inventors succeeded in synthesizing novel compounds of Chemical Formulas 1 and 2, which have a long drug action period of time and show cardiotonic and hypotensive action, as disclosed in Korean Pat. No. 148,755. In addition, these novel compounds were also found to have potent action for increasing myocardial contractile force and heart rate in an experiment using isolated rat heart preparations, for dilating the isolated blood vessels which are contracted with phenylephrine, and for increasing heart rate and decreasing blood pressure in an experiment using rabbits, as reported by the present inventors (Lee, Y. S. et al.).

In current use as therapeutics for congestive heart failure are digitalis cardiac glycosides and dopamines. Digitalis cardiac glycosides have an advantage of being suitable for oral administration, but are disadvantageous in that they have so a narrow safety margin that they are dangerous to use and cause arrhythmia. Sympathomimetic drugs, such as dopamine and dobutamine, are effective as therapeutic agents for congestive heart failure, but there are some shorcomings that they must be intravenously infused and their use causes the down regulation of the β-adrenoceptor.

A good therapeutic effect may be attained in patients suffering from heart failure by co-administration of cardiotonic drugs capable of increasing the lowered myocardial contractile force, and the drugs which can reduce the burden overloaded to the heart through vasodilation or by prevention of thrombogenesis for smooth blood circulation. Thus, because digitalis cardiac glycosides or dopamine have only cardiotonic activity, they can show a good therapeutic effect when being administered along with a vasodilator (hypotensive agent) and a platelet aggregation inhibitor. Such co-administration of various drugs, however, has a problem in that the drugs administered are interacted to affect the adsorption and drug metabolism of each drug in the body, so as to increase the frequency of side effect occurrence.

From various evidences, it has been disclosed that oxygen free radicals excessively generated, including NO, act as one of the major factors causing acute and chronic tissue/organ injury. The above tissue/organ injuries can be exemplified by the tissue injury upon re-perfusion for inflammatory diseases such as arthritis, myocardial infarction, cerebral apoplexy, or ischemic diseases or by the complex organ injury due to endotoxins derived from bacterial infection. Accordingly, much attention has been paid to developing the materials, suppressive of the expression of iNOS or inhibitory of mass production of NO, which can be used for treating various diseases caused by a large quantity of NO. These materials, also are expected to protect the myocardial injury due to, for example, acute cardiac infarction or ischemic cardiac diseases, thereby suppressing the aggravation of heart failure or curing it.

DISCLOSURE OF THE INVENTION

With the above problems in mind, the present inventors found, as, a result of active research, that the compounds of Chemical Formulas 1 and 2 are useful as therapeutic agents for heart failure by virtue of their expressing heart stimulating action, vasodilation (hypotensive action), anti-platelet aggregation and iNOS inhibition at once and in combination as well as a therapeutic agent for the treatment of thrombosis by taking advantage of their inhibitory activity against platelet aggregation and as a therapeutic agent for NO-mediated tissue injury, septicemia, and DIC by virtue of their suppressive activity against iNOS expression and NO synthesis.

Therefore, it is an object of the present invention to provide a therapeutic composition for the prophylaxis and treatment of heart failure, thrombosis, iNOS-induced tissue injury, septicemia, and DIC.

Based on the present invention, the above object could be accomplished by a provision of a pharmaceutical composition comprising, as a pharmacologically effective ingredient, 1-α-naphthylmethyl-6,7-dihydroxy-1,2,3,4-tetrahydroisoquinoline and/or 1-β-naphthylmethyl-6,7-dihydroxy-1,2,3,4-tetrahydroisoquinoline, each of them showing heart stimulating activity, hypotensive activity, inhibitory activity against platelet aggregation, and suppressive activity against iNOS expression in combination and at once, represented by the following Chemical Formulas 1 and 2, respectively,:

Chemical Formula 1

Chemical Formula 2

BRIEF DESCRIPTION OF THE FIGURES

The above and other objects, features and other advantages of the present invention will be more clearly understood from the following detailed description taken in conjunction with the accompanying figures, in which.

Lane 3: LPS (300 ng/ml)+Compound of Chemical Formula 1 (10:μM)

Lane 4: LPS (300 ng/ml)+Compound of Chemical Formula 1 (30:μM)

Lane 5: LPS (300 ng/ml)+Compound of Chemical Formula 1 (100:μM)).

Lane 3: LPS (100 ng/ml)+IFN-γ(10 U/ml)+Compound of Chemical Formula 2 (1:μM)

Lane 4: LPS (100 ng/ml)+IFN-γ(10 U/ml)+Compound of Chemical Formula 2 (10:μM)

Lane 5: LPS(100 ng/ml)+IFN-γ(10 U/ml)+Compound of Chemical Formula 2 (100:μM).

-Δ-: LPS(20 mg/kg)+Compound of Chemical Formula 1 (10 mg/kg)

-□-: LPS(20 mg/kg)+Compound of Chemical Formula 1 (20 mg/kg)); and

-Δ-: LPS(20 mg/kg)+Compound of Chemical Formula 2 (10 mg/kg)

-□-: LPS(20 mg/kg)+Compound of Chemical Formula 2 (20 mg/kg)).

DETAILED DESCRIPTION OF THE INVENTION

In the present invention, there are provided novel uses of the THI compounds, 1-α-naphlthylmethyl-6,7-dihydroxy-1, 2,3,4-tetrahydroisoquinoline and 1-β-naphthylmethyl-6,7-dihydroxy-1,2,3,4-tetrahydroisoquino-line, represented by Chemical Formulas 1 and 2, in the treatment and/or prophylaxis of heart failure, thrombosis, iNOS-induced tissue injury, septicemia, and DIC.

The compounds of Chemical Formulas 1 and 2 may have many isomers. For instance, as seen in Chemical Formulas 1 and 2, tautomers may be-present. Also, because each of the compounds of Chemical Formulas 1 and 2 contains at least one asymmetric carbon, the compounds can exist as an optically pure (R)- or (S)-isomer, as a mixture with unequal proportions of (R)- and (S)-isomers, or as a racemic form.

Therefore, it should be noted that all isomers of the compounds of Chemical Formulas 1 and 2 are within the scope of the present invention., Also, pharmaceutically acceptable salts of the compounds of Chemical Formulas 1 and 2 and their prodrugs are included within the present invention.

Concrete examples of the acids useful to prepare, the pharmaceutically acceptable salts of the compounds of Chemical Formulas 1 and 2 include hydrochloric acid, bromic acid, sulfuric acid, methanesulfonic acid, propionic acid, succinic acid, glutaric acid, citric acid, fumaric acid, maleic acid, tartaric acid, glutamic acid, gluconic acid, glucuronic acid, galaturonic acid, ascorbic acid, carbonic acid, phosphonic acid, nitric acid, acetic acid, L-aspartic acid, lactic acid, vanillic acid and hydroiodic acid.

As mentioned above, prodrugs of the compounds of Chemical Formulas 1 and 2 are also within the scope of the present invention. With the ability to be easily converted into pharmacologically active forms in the body, these prodrugs are reactive derivatives of the compounds of Chemical Formulas 1 and 2. A reference directed to the selection and preparing processes of suitable prodrugs is Design of Prodrug, ed. H. Bundgarrd, (1985).

1-α-naphthylmethyl-6,7-dihydroxy-1,2,3,4-tetrahydroisoquinoline represented by Chemical Formula 1, or 1-β-naphthylmethyl-6,7-dihydroxy-1,2,3,4-tetrahydroisoquinoline represented by Chemical Formula 2, shows heart stimulation, hypotensive action, anti-platelet aggregation, and iNOS inhibition, in combination and at once, so that a pharmaceutical composition comprising at least one of the compounds as an effective ingredient can be used as a heart failure preventive or curative.

At present, in order to cure heart failure, digitalis agents, cardiac glycosides, vasodilators, calcium antagonists, and angiotensin converting enzyme (ACE) inhibitors are clinically used, alone or in combination, with the expectation of hemodynamic improvement by reducing both preload and afterload to the heart. In this regard, the compounds of Chemical Formulas 1 and 2, according to the present invention, can be used as effective therapeutic agents for heart disease because they are inodilators which show heart stimulating action and vasodilation at once.

Heart failure is aggravated when circulatory diseases such as arteriosclerosis and hyper-tension last for a long period of time to impose a heavy burden on the heart or when coronary artery diseases induced by thrombus, or ischemic diseases, such as cardiac infarction, take place. Those who show high risk indices in heart diseases are actively recommended to continually take platelet aggregation inhibitors with the aim of the prevention or prophylaxis of various heart or circulatory diseases. Hence, the compounds of Chemical Formulas 1 and 2, according to the present invention, have antithrombotic activity by virtue of their inhibitory action against platelet aggregation, satisfying a requirement for a curative for heart failure. Patients suffering from chronic heart failure are in an elevated immunoactive state and have the expression.of iNOS activated in the intestines and the blood vessels. In this connection, a large amount of NO is synthesized from INOS expression, which may form peroxinitrite resulting in reducing myocardial contractile force and tissue injury. The compounds of Chemical Formula 1 and 2 inhibit the expression of iNOS and thus, the synthesis of NO and tissue injury thereby. That is, in addition to restraining the tissue injury of NO, the compounds of the present invention inhibit the generation of the oxygen free radical, one of the factors to cause the lowering of the myocardial contractive force of chronic heart failure patients. Consequently, the compounds of Chemical Formulas 1 and 2 express the above various activities, in combination and at once, so that they can be used as therapeutic agents exceptionally improved in treating heart failure.

Herein, the term "therapeutic agent for heart failure" means a drug which can inhibit the aggravation of heart failure caused by the hypofunction of myocardial contraction due to acute myocardial infarction, the hypofunction of myocardial contraction due to an increase of immune activity according to, for example, chronic inflammation, the hypofunction of myocardial contraction due to ischemic heart diseases, or the hypofunction of myocardial contraction due to congestive heart failure, such as prolonged hypertension, arteriosclerosis, or coronary artery diseases, or can cure such heart failure.

With the antithrombotic activity through platelet aggregation inhibition, and the iNOS inhibitory activity, either of the compounds of Chemical Formulas 1 and 2 can be contained as an effective ingredient in a pharmaceutical composition which is useful as an antithrombotic agent, a tissue injury inhibitor, a septicemia curative, and/or a therapeutic agent for DIC.

The antithrombotic agent prevents the formation of thrombus after operation, inhibits the aggravation of thrombosis or embolus-induced diseases, such as ischemic cerebral vascular accidents, coronary artery diseases, ischemic myocardial infarction, and chronic arterial infarction, or cures such diseases.

The tissue injury inhibitor prevents or cures the tissue injury caused by NO, clearly driven from iNOS synthesis, which is developed into, for example, inflammatory diseases such as arthritis, and the tissue injury due to ischemic diseases, such as arteriosclerosis, myocardial infarction and cerebral apoplexy, and due to re-perfusion, or inhibits the aggravation of such tissue injury.

The septicemia curative is to treat DIC and the septicemia caused by complex tissue injury The therapeutic agent for DIC is to treat the syndromes caused by the activation of blood coagulation, such as rapid decrease in the number of platelets, bleeding, shock, thrombosis, and vascular infarction.

The pharmaceutical composition of the present invention may be administered via parental, oral, intravenous or rectal routes and have a dosage form, such as selected from a parenteral solution, a capsule, a pill, a sugar-coated tablet, a suppository, a solution, a suspension, or an emulsion.

To prepare the pharmaceutical compositions, the compounds of the present invention may be mixed with pharmaceutically acceptable carriers, such as organic or inorganic, solid, semi-solid, or liquid diluents or excipients. If necessary, an auxiliary, a stabilizer, a wetting agent or emulsifier, a buffer and/or other ordinary additives may be contained in the pharmaceutical composition of the present invention.

An experiment shows that, even when being orally administered, the compounds of the present invention retain high levels in blood for a significantly long period of time. Based on the data of the experiment, the compounds of the present invention may be administered at a dose of 0.01–20 mg per kg of body weight upon injection and 2–200 mg per kg of body weight upon oral administration.

In a toxicity experiment, the compounds of the present invention are found to have a 50% lethal dose ($LD_{50}$) of at least 1,000 mg/kg upon oral administration. When being intraperitoneally injected, 1-α-naphthylmethyl-6,7-dihydroxy-1,2,3,4-tetrahydroisoquinoline represented by Chemical Formula 1 has an $LD_{50}$ of 290.0 mg/kg with a 95% confidence limit ranging from 235.1 to 359.9 mg/kg while 1-β-naphthylmethyl-6,7-dihydroxy-1,2,3,4-tetrahydroisoquinoline has an $LD_{50}$ of 438.6 mg/kg with a 95% confidence limit ranging from 350.9 to 548.2 mg/kg.

In the present invention, 1-α-naphthylmethyl-6,7-dihydroxy-1,2,3,4-tetrahydroisoquinoline of Chemical Formula 1 and 1-β-naphthylmethyl-6,7-dihydroxy-1,2,3,4-tetrahydroisoquinoline of Chemical Formula 2 are assayed for the above-mentioned pharmacological effects and evaluated as showing such various effects in combination.

Also, the compounds of the present invention are compared with higenamine, expected to have similar actions, in various experiments. From the results of the experiments, the compounds of Chemical Formulas 1 and 2 are concluded to have a potent inhibitory activity against platelet aggregation induced by epinephrine rather than by adenosine diphosphate (hereinafter referred to as "ADP") or collagen. In addition, with the antagonistic effects on α-adrenoceptors, the compounds of the present invention are believed to dilate blood vessels and inhibit platelet aggregation, as well.

Suppression of the expression of iNOS induced by endotoxins and the synthesis of NO, the compounds of Chemical Formulas 1 and 2 show dose-dependent effects. By inhibiting the tissue injury due to NO synthesis, the compounds of the present invention can be used as a preventive, inhibitive or curative against inflammatory diseases such as arthritis, various ischemic diseases such as cerebral apoplexy and myocardial infarction, and the tissue injury generated upon re-perfusion. Also, the compounds of the present invention can be applied for the treatment of the diseases caused by rapid complex tissue injury, such as septicemia and DIC.

In an in vivo experiment using mice and rats, the compounds of Chemical Formulas 1 and 2 are demonstrated to have superior antithrombotic activity in terms of significantly lowering the mortality due to acute thrombosis and inhibiting thrombosis in the arterio-venous shunt (AVS) tubes.

Endotoxins such as LPS induce various DICs. Examples of the indications for DICs include a decrease in the number of platelets in blood, a decrease of fibrinogen level and an increase of fibrin/fibrinogen degradation product (FDP) level in blood, and an extension of prothrombin time (PT) and activated partial thromboplastin time (aPTT). These indices for LPS-induced DIC can be improved by the compounds of the present invention. That is, when being administered, the compounds of the present invention prevent the decrease of the number of platelets and the concentration of fibrinogen in blood, the increase of FDP level, and the extension of PT and aPTT induced by LPS. Meanwhile, endotoxins are also known to cause an increase in the level of serum glutamic-oxaloacetic transaminase (S-GOT), serum glutamic-pyruvic transaminase (S-GPT) and blood urea nitrogen (BUN). In this regard, the compounds of the present invention can be used for preventing LPS from causing an increase in S-GOT, S-GPT and BUN level. That is, various indices for the LPS-induced multiple organ failure (MOF) are improved by the compounds of the present invention. Further, due to the activity of lowering LPS-induced mortality, the compounds of the present invention are recognized to be protective of the shock caused by the endotoxin.

A better understanding of the present invention may be obtained in light of the following examples which are set forth to illustrate, but are not to be construed to limit the present invention.

EXPERIMENTAL EXAMPLE 1

Inhibitory Effects on Platelet Aggregation

For experiment, a blood platelet concentrate which was purchased from the Blood Bank of the Seoul National University Hospital, Korea, was measured for the number of platelets with the aid of a platelet analyzer (PLT-4, Texas Instruments), and diluted with phosphate buffered saline (hereinafter referred to as "PBS") to give platelet rich plasma (hereinafter referred to as "PRP") which ranged, in platelet number, from $300 \times 10^6$ to $400 \times 10^6$/ml. After being incubated at 37° C. for 3 min, PRP was added with ADP, collagen or epinephrine to induce platelet aggregation. The reduction in turbidity of PRP was observed and the degree of aggregation was monitored using a platelet aggregometer, such as that manufactured by Chrono-Log Corp. U.S.A., identified as "Model 500VS".

The inhibitory activities of sample compounds against the platelet aggregation were evaluated as the % inhibition calculated according to the following equation:

% Inhibition=$(A-B)/A \times 100$ wherein
  A: aggregation degree of platelets obtained when adding a platelet aggregation inducer alone;
  B: aggregation degree of platelets obtained when adding a combination of a platelet aggregation inducer and a sample.

Obtained using human platelets, the inhibitory effects of the compounds of Chemical Formulas 1 and 2 on platelet aggregation are given, along with the results from the control higenamine, in Table 1, below.

TABLE 1

Inhibitory Effect on Platelet Aggregation of the Compounds and Higenamine

| | $IC_{50}$ (M) | | |
|---|---|---|---|
| | ADP | Collagen | Epinephrine |
| Higenamine | >1 × 10$^{-3}$ | 7.0 × 10$^{-5}$ | 1.9 × 10$^{-5}$ |
| Compound 1 | 7.3 × 10$^{-4}$ | 9.2 × 10$^{-5}$ | 3.4 × 10$^{-6}$ |
| Compound 2 | 8.6 × 10$^{-4}$ | 9.6 × 10$^{-6}$ | 6.0 × 10$^{-6}$ |

Note:
ADP: 1 × 10$^{-3}$ M; Collagen: 2–4 × 10$^{-6}$ g/ml; Epinephrine: 2 × 10$^{-6}$ M As recognized from the data of Table 1, as much as $1 \times 10^{-3}$ M of higenamine shows no inhibitory activity against the ADP-induced platelet aggregation while, weak as they are, the compounds of Chemical Formulas 1 and 2 have an $IC_{50}$ of $7.3 \times 10^{-4}$ M and $8.6 \times 10^{-4}$ M, respectively. Compared to the action of collagen, the compound of Chemical Formula 1 has inhibitory activity as measured at $IC_{50}$ of $9.2 \times 10^{-5}$ M, which is similar to that of higenamine. However, the compound of Chemical Formula 2 is more potent in the inhibitory activity by about ten times than the compound of Chemical Formula 1 and higenamine. As for epinephrine-induced platelet aggregation, the compounds of Chemical Formulas 1 and 2 have an $IC_{50}$ of $3.4 \times 10^{-6}$ and $6.0 \times 10^{-6}$, respectively, which demonstrate that the compounds are of more potent activity than higenamine whose $IC_{50}$ was measured to be $1.9 \times 10^{-5}$ M. To sum up, the compounds of Chemical Formulas 1 and 2 show higher potency than does higenamine in inhibitory activity against the platelet aggregation induced by ADP or epinephrine. In inhibitory activity against collagen-induced platelet aggregation, the compounds of Chemical Formulas 1 and 2 are similar to or more potent than higenamine.

EXPERIMENTAL EXAMPLE II

Binding Affinity to α-Adrenoceptor

To investigate whether the compounds of the present invention competitively bind to α-receptors to exhibit the above-illustrated inhibitory activity against platelet aggregation and to show vasodilation, rat cerebral cortical membrane rich in α-receptors was prepared. For this, the cerebral cortex obtained from rats (Sprague-Dawley, 250±20 g; unless particularly mentioned, the same rats were used in the following experiments) was homogeneously mixed with a 20× buffer (50 mM Tris, 5 mM MgSO$_4$, 1 mM EDTA, 1 mM ascorbic acid, pH 7.7) and then, centrifuged three times at 35,000×g for 15 min and the pellet was stored at −70° C. A solution of 5 mg of the pellet in 1 ml of the buffer was incubated, along with [$^3$H]prazosin (200 pM) and samples, at 25° C. for 30 min followed by adding 10 ml of a buffer (50 mM Tris, pH 7.7) to quench the binding reaction. The resulting solution was filtered through a Whatman GF/C glass microfiber filter which was then shaken for 2 hours while being completely submerged in a scintillation cocktail. The radioactivity was measured using a scintillation counter (Beckman, LS6500)

TABLE 2

Dissociation Constants ($K_i$) for Cerebral α-Receptor of Rat and $IC_{50}$ in Rat thoracic aorta

| Compounds | Ki (M) | $IC_{50}$ (M) |
|---|---|---|
| Higenamine | 1.26 × 10$^{-6}$ | 1.02 × 10$^{-6}$ |
| Compound 1 | 0.27 × 10$^{-6}$ | 2.75 × 10$^{-6}$ |
| Compound 2 | 0.15 × 10$^{-6}$ | 2.81 × 10$^{-6}$ |

From the binding of prazosin to the α-receptor, there were obtained a $K_d$ value of 133.5±8.91 pM and a $B_{max}$ value of 15.15±0.64 fmol/mg. The sample compounds were found to have affinity for α-receptor as measured for the dissociation constant values ($K_i$) ranging from 0.15 to 1.25:μM. In addition, the approximation between these measured dissociation constant values and the $IC_{50}$ values (1.02–2.81:μM) measured in the phenylephrine-contracted isolated aorta and the inhibitory concentration values ($IC_{50}$: 3.4–19:μM) against epinephrine-induced platelet aggregation also demonstrate that the compounds of the present invention block ax-receptors to dilate the blood vessels and to inhibit platelet aggregation.

EXPERIMENT EXAMPLE III

Suppression of LPS-induced iNOS mRNA Expression in Rat Isolated Aorta

Rats were anesthetized with pentobarbital sodium (50 mg/kg) and the aorta was isolated, followed by removing endothelium from the aorta. After being incubated at 37° C. for 8 hours in a Krebs solution containing 300 ng/ml of LPS, the aorta was subjected to total RNA extraction with the aid of a trizol solution (GibcoBRL). After quantification by use of a UV spectrophotometer (Shimadzu, UV-1201), the total RNA obtained was electrophoresed on a formamide-formaldehyde agarose gel and transferred to a nylon membrane. Thereafter, the total RNA on the nylon membrane was hybridized with cDNA probes for iNOS to determine the expression level of iNOS mRNA, in which the cDNA of iNOS was labeled with $^{32}$P-dCTP by a random-primer method. For quantification, an x-ray film was exposed to the radioactive irradiation from the nylon membrane and developed to compare the dot sizes of desired objects with those of GAPDH (glyceraldehyde-3-phosphate dehydrogenase).

Figure 1:
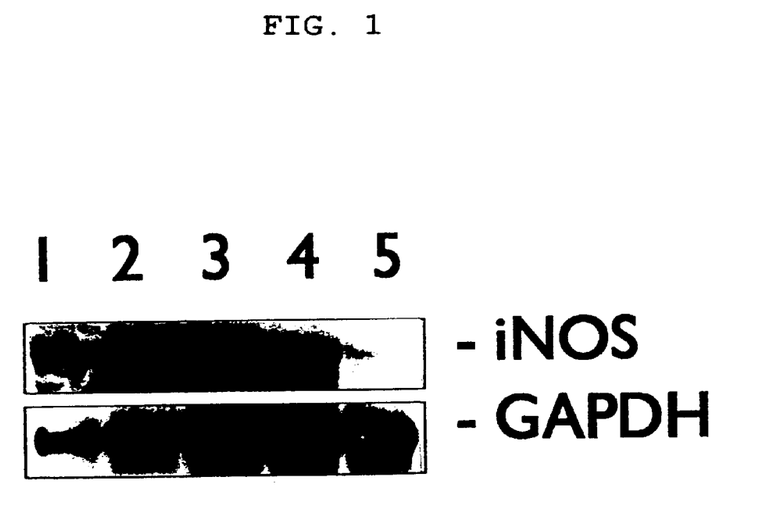
FIG. 1 is an autoradiogram of Northern blot which shows that the compound of Chemical Formula 1 suppresses the expression of iNOS mRNA in isolated rat aorta stimulated by LPS for 8 hours in vitro, in which Lane 1: control Lane 2: LPS (300 ng/ml)

When aortic preparations were incubated, in vitro, the blood vessel was cultured, in vitro, in the presence of LPS, iNOS mRNA was transcribed in a large amount. However, the additional presence of the compound of Chemical Formula 1 in the culture did not allow the iNOS mRNA to be expressed. These results are given in FIG. 1 which shows Northern blots for iNOS mRNA obtained after the aortae were incubated along with LPS and/or the compound of Chemical Formula 1. In the autoradiogram of Northern blot, lanes 3, 4 and 5 show the iNOS mRNA expression under the influence of the compound of Chemical Formula 1 at its different concentrations (10:$\mu$M, 30:$\mu$M and 100:$\mu$M, respectively) while lanes 1 and 2 show a control (aorta alone) and the influence of LPS (300 ng/ml) only, respectively. As shown in FIG. 1, the iNOS mRNA is strongly expressed in the LPS treated group (lane 2), but, the compound of Chemical Formula 1 inhibits the LPS-induced iNOS mRNA expression in a concentration-dependent manner (lanes 3, 4 and 5).

EXPERIMENTAL EXAMPLE IV

Suppressive Effect on LPS- and IFN-γ-induced iNOS mRNA Expression in Macrophage

In a DMEM medium supplemented with thermally treated 10% fetal calf serum, penicillin (100 U/ml) and streptomycin (100 mg/ml), macrophages (RAW 264.7 cells) were cultured to be confluent in a $CO_2$ incubator. After being transferred to a serum-free DMEM medium, the cells were cultured for additional 24 hours and then, further for 18 hours in the presence of LPS (100 ng/ml) and interferon-γ (hereinafter referred to as "IFN-γ"; 10 U/ml), and/or the compound of Chemical Formula 2 (0, 1, 10, and 100:$\mu$M). Using a trizol solution, the total RNA was extracted from the cultured macrophages. After quantification in a spectrophotometer, the total RNA obtained was electrophoresed on a formamide-formaldehyde agarose gel and transferred to a nylon membrane. Thereafter, the total RNA on the nylon membrane was hybridized with cDNA probes for iNOS to determine the expression level of iNOS mRNA, in which the cDNA of iNOS was labeled with $^{32}$P-dCTP by a random-primer method. For quantification, an x-ray film was exposed to the radioactive irradiation from the nylon membrane and developed to compare the radioactivity level of desired objects with those of GAPDH.

Figure 2:
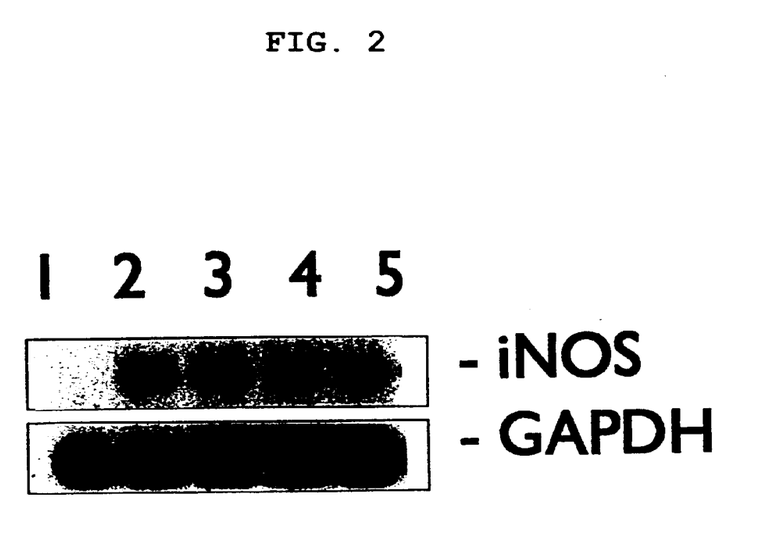
FIG. 2 is an autoradiogram of Northern blot which shows that the compound of Chemical Formula 2 suppresses the expression of INOS mRNA stimulated by LPS and IFN-γ in macrophages (RAW 264.7 cells) in which Lane 1: control Lane 2: LPS (100 ng/ml)+IFN-γ(10 U/ml)

These results are given in FIG. 2 which shows Northern blots for iNOS mRNA obtained after macrophages were cultured along with LPS and IFN-γ and/or the compound of Chemical Formula 2. In the autoradiogram of Northern blot, lanes 3, 4 and 5 show the iNOS mRNA expression under the influence of the compound of Chemical Formula 2 at its different concentration level (1:$\mu$M, 10:$\mu$M and 100:$\mu$M, respectively) while lanes 1 and 2 show a control (cell alone) and the influence of LPS (100 ng/ml) and IFN-γ. As shown in FIG. 2, when the macrophages were cultured for 18 hours in the presence of LPS (100 ng/ml) and IFN-γ (10 U/ml), the iNOS mRNA was expressed. On the other hand, the compound of Chemical Formula 2 inhibits the LPS/IFN-γ-induced iNOS mRNA expression in a concentration-dependent manner (lanes 3, 4 and 5).

EXPERIMENTAL EXAMPLE V

Suppressive Effect on LPS- and IFN-γ-induced NO Synthesis in Macrophage

In a DMEM medium supplemented with thermally treated 10% fetal calf serum, penicillin (100 U/ml) and streptomycin (100 mg/ml), macrophages (RAW 264.7 cells) were cultured to be confluent in a $CO_2$ incubator. After being transferred to a serum-free DMEM medium, the cells were cultured for additional 24 hours and then, further for 18 hours in the presence of LPS (100 ng/ml) and IFN-γ, and either of the compounds of Chemical Formulas 1 and 2 (0, 1, 10, and 100:$\mu$M). The amount of the NO synthesized was measured indirectly through the amount of nitrite, an oxidation product of NO. To this end, the nitrite was subjected to color reaction with the Griess reagent (0.1% naphthyl-ethylenediamine dihydrochloride, 1% sulphanilamide, 5% phosphate solution) and its absorbance at 550 nm was measured by a spectrophotometer. The amounts of the nitrite were measured using $NaNO_2$ as a standard, and the results are given in Table 3, below.

TABLE 3

Suppressive Effect on LPS- and IFN-γ-induced NO Synthesis in Macrophage

| | Concentration of Nitrite (:$\mu$M) | |
| --- | --- | --- |
| | Compound 1 | Compound 2 |
| Control | 8 ± 0.1 | 8 ± 1.1 |
| LPS + IFN-γ | 57 ± 3.3 | 57 ± 4.2 |
| Compound 1: $\mu$M + LPS + IFN-γ | 30 ± 2.9 | 34 ± 3.1 |
| Compound 10: $\mu$M + LPS + IFN-γ | 25 ± 3.4 | 22 ± 2.8 |
| Compound 100: $\mu$M + LPS + IFN-γ | 9 ± 3.0 | 11 ± 2.0 |

As apparent from the data of Table 3, when the macrophages were cultured in the presence of the endotoxin, large amount of nitrite was detected, indicating the mass synthesis of NO. From the control, which was added with none of the endotoxin and IFN-γ, 8:$\mu$M of nitrite was detected. On the other hand, as much as 57 :M of nitrite was measured from the culture added with the endotoxin and IFN-γ. Together with both of the LPS and IFN-γ, either of the compounds of Chemical Formulas 1 and 2, was added at an concentration of 1:M to the culture, the amount of the nitrite synthesized was measured to be 30:$\mu$M or 34:$\mu$M, both of which are smaller than the amount measured upon the co-existence of LPS and IFN-γ. Also, smaller amounts of nitrite were detected when using higher concentrations of either of the compounds of Chemical Formulas 1 and 2, which indicates that the compounds of Chemical Formulas 1 and 2 powerfully inhibit the NO synthesis caused by the endotoxin in a concentration-dependent manner.

EXPERIMENTAL EXAMPLE VI

Inhibitory Effects on Acute Thrombosis-caused Death in Mice

A mixture of collagen (300:$\mu$g/kg) plus epinephrine (30:$\mu$g/kg) was injected into the tail vein of mice (ICR; 20±20 g, the same mice were employed in all of the following experiments) to induce massive, acute thrombosis in the pulmonary artery. Thus, an acute thrombosis model, in which mice were paralyzed in 1–3 min after the injection and most of them died within 15 min was prepared. To investigate the effect of the compounds of Chemical Formulas 1 and 2 on the acute thrombosis, either of the compounds was orally administered to mice for 1 or 3 days. The intravenous injection of the mixture of collagen and epinephrine was conducted 1 hour after the final oral administration. An observation was taken to examine the mortality change and the recovery from the paralysis and the results are given in Tables 4 and 5, below.

TABLE 4

Recovery Rate from the Paralysis due to Thrombus Formation

| Sample Compounds. | Dose (mg/kg) | Total Nos. Of Mice | Mice Recovered* Number | % |
|---|---|---|---|---|
| Control | — | 60 | 13 | 17 |
| Aspirin | 50 | 53 | 32 | 52 |
| Higenamine | 50 | 30 | 11 | 37 |
| | 100 | 27 | 13 | 48 |
| Compound 1 | 50 | 17 | 8 | 47 |
| | 100 | 20 | 9 | 45 |
| Compound 2 | 50 | 28 | 14 | 50 |
| | 100 | 24 | 12 | 50 |

*Mice recovered from thrombotic paralysis within 15 min.
Each sample was administered orally once.

TABLE 5

Recovery Rate from the Paralysis due to Thrombus Formation

| Sample Compounds. | Dose (mg/kg) | Total Nos. of Mice | Mice Recovered* Number | % |
|---|---|---|---|---|
| Control | — | 20 | 4 | 20 |
| Aspirin | 50 | 20 | 11 | 55 |
| Higenamine | 10 | 12 | 2 | 17 |
| | 50 | 11 | 5 | 45 |
| Compound 1 | 10 | 10 | 3 | 30 |
| | 50 | 12 | 5 | 42 |
| Compound 2 | 10 | 10 | 7 | 70 |
| | 50 | 11 | 7 | 64 |

*Mice recovered from thrombotic paralysis within 15 min.
Each sample was administered orally once for three successive days.

Most of the mice were paralyzed within 1 min after the injection, following dilation of the pupils, difficult breathing, and convulsions. Most of the mice either died within 5 min or were subjected to paralysis for 15 min or longer. Only a few of them recovered from the paralysis.

As shown in Tables 4 and 5, only 17–20% of the control group which was administered with a mixture of collagen and epinephrine, but not with the sample compounds, were recovered from the paralysis within 15 min and moved freely. Aspirin and higenamine, which were used as positive controls, showed a recovery rate of 52% and 37 %, respectively, when both of them were administered orally once at a dose of 50 mg/kg. A dose of 100 mg/kg of higenamine increased the recovery rate up to 48% when being administered once. As for the compounds of Chemical Formulas 1 and 2, they showed similar recovery rates to that of aspirin when being administered at a dose of 50 mg/kg or 100 mg/kg once. However, when being administered at a dose of 10 mg/kg or 50 mg/kg once a day for successive three days, the compound of Chemical Formula 2 had an advantage over aspirin, raising the recovery rate to 64–70%.

EXPERIMENTAL EXAMPLE VII

Inhibitory Effect on Thrombus Formation in Arterio-venous Shunt Tube

An AVS tube was prepared. For this, a scalp vein set was cut into a length of 18 cm, and each end was connected to a 18G syringe needle while a 100% cotton thread 5 cm long was fixed to the center of the tube. Rats were anesthetized with ketamine (250 mg/kg) by injection (i.m.) and underwent laparotomy. An AVS tube filled with saline was installed between the abdominal aorta and the renal vein in such a way that its one syringe needle was inserted in the abdominal aorta and the other syringe needle was inserted in the renal vein. Blood was allowed to pass through the AVS tube so as to form thrombus on the cotton thread. After circulation of blood through the AVS tube for 15 min, the thread was taken out from the AVS tube. The weight of the thrombus formed on the cotton thread was determined by weighing the thread. The inhibitory effects of orally administered sample compounds on thrombus formation were observed in rats and the results are given in Tables 6 and 7.

TABLE 6

Inhibitory Effects on Thrombus Formation in AVS Tube Inserted in Rat Orally Administered Once with Various Drugs

| Compounds | Dose (mg/kg) | Total Nos. of Rats | Weights (mg) | % Inhibition |
|---|---|---|---|---|
| Control | — | 4 | 33.61 ± 7.620 | |
| Aspirin | 50 | 6 | 19.89 ± 7.213* | 40.8 |
| Higenamine | 25 | 8 | 22.98 ± 11.271 | 31.6 |
| Compound 1 | 25 | 8 | 20.27 ± 5.366** | 39.7 |
| Compound 2 | 25 | 8 | 22.68 ± 10.127 | 32.5 |
| Control | — | 9 | 39.54 ± 5.625 | |
| Aspirin | 50 | 7 | 25.18 ± 6.725*** | 36.3 |
| Higenamine | 50 | 8 | 29.61 ± 5.059** | 25.1 |
| Compound 1 | 50 | 8 | 29.72 ± 5.975** | 24.8 |
| Compound 2 | 50 | 6 | 28.58 ± 4.234*** | 27.7 |

*$p < 0.051$,
**$p < 0.01$,
***$p < 0.001$

TABLE 7

Inhibitory Effects on Thrombus Formation in AVS Tube Inserted in Rat Orally Administered Once a Day for Successive Three Days with Various Drugs

| Compounds | Dose (mg/kg) | Total Nos. of Rats | Weight (mg) | % Inhibition |
|---|---|---|---|---|
| Control | — | 8 | 42.67 ± 5.381 | |
| Aspirin | 50 | 9 | 37.37 ± 7.369 | 12.4 |
| Higenamine | 10 | 12 | 36.76 ± 7.964 | 13.9 |
| | 50 | 12 | 34.68 ± 8.513* | 18.7 |
| Compound 1 | 10 | 11 | 31.78 ± 8.385** | 25.5 |
| | 50 | 11 | 30.72 ± 6.334*** | 28.0 |
| Compound 2 | 10 | 11 | 32.24 ± 4.836*** | 24.4 |
| | 50 | 9 | 30.18 ± 6.571*** | 29.3 |

*$p < 0.05$,
**$p < 0.01$,
***$p < 0.001$

The weight of the thrombus formed inside the AVS tube was significantly influenced by the weather conditions (atmospheric pressure, humidity, etc.) on the day of experiment. For effective analysis, aspirin, an antithrombotic agent, was administered (50 mg/kg) as a positive control. In a negative control which was administered with no drugs, thrombus was formed at an amount of 33–42 mg. A one-time administration of aspirin, at a dose of 50 mg/kg resulted in an inhibitory effect on thrombus formation by 36–40%. When being administered once at both doses of 25 mg/kg and 50 mg/kg, higenamine showed a % inhibition from 25 to 31%. On the other hand, the compounds of Chemical Formulas 1 and 2 inhibited thrombus formation by 24–39% upon being administered once at both doses of 25 mg/kg and 50 mg/kg. From this result, it is apparent that the compounds of the present invention have inhibitory activity against thrombus formation, which is similar to or more potent than that of higenamine.

In the case of the administration for successive three days, a dose of 50 mg/kg of aspirin decreased thrombus formation by as little as 12%. Where an average-exceeding amount of thrombus was formed in the AVS tube of the control, according to weather conditions on the day of experiment, the inhibitory effects of test drugs on thrombus formation were relatively low. Hence, comparison between test drugs and a positive control (aspirin-administered group) was indispensable for accurate analysis.

When being administered at both doses of 10 mg and 50 mg once a day for three successive days, higenamine showed a % inhibition of 13–18%, which was similar to that of aspirin. For the compounds of Chemical Formulas 1 and 2, both doses of 10 mg/kg and 50 mg/kg decreased thrombus formation by about 24% and 28%, respectively. These data indicate that the compounds of the present invention have advantages over aspirin or higenamine in terms of inhibitory activity against thrombus formation.

EXPERIMENTAL EXAMPLE VIII

Improvement Effect on Indices for Bacterial Endotoxin-induced DIC and MOF in Rats Rats (Sprague-Dawley, 250±50 g) were anesthetized with ketamine (250 mg/kg) by injection (i.m.). 30 min later, LPS (20 mg/kg) was infused into the tail vein of the rats over a 3 hour period. Thereafter, blood was harvested from the artery and measured for platelet number, PT, aPTT, fibrinogen level, FDP level, and the levels of S-GOT, S-GPT and BUN. Test drugs were orally administered once a day for two days. One hour after the final administration of the compounds of interest, the rats were anesthetized.

As an anticoagulant, sodium citrate was used. The number of platelets in the blood was measured by use of a platelet counter. Anticoagulant-treated blood was centrifuged at 1,500×g for 10 min and the plasma was obtained for testing.

In order to obtain a prothrombin time (PT), 100 µl of the plasma was added with 50 µl of a thromboplastin reagent (Sigma, U.S.A.) and a clotting time was measured by use of a fibrometer (Becton Dickinson Co., Canada). Before mixing, the plasma and thromboplastin reagent were pre-incubated at 37° C. for 3 min and 5 min, respectively.

For measurement of the aPTT, 100 µl of the plasma was incubated at 37° C. for 3 min and added with 100 µl of an activated partial thromboplastin time reagent (Sigma U.S.A.) and 100 µl of 0.02 M $CaCl_2$ and a clotting time was measured by use of a fibrometer. Before addition, the reagent was pre-incubated at 37° C. for 1 min while $CaCl_2$ was pre-warmed at 37° C.

To determine the fibrinogen level, first, 20 µl of the plasma was mixed with 180 µl of a buffer and incubated at 37° C. for 2 min. To this solution was added 100 µl of a thrombin reagent (Sigma U.S.A.), followed by measuring a clotting time. Then, the fibrinogen level was determined from a calibration curve obtained with a fibrinogen reference.

The FDP level was determined by use of the Thrombo-Wellcotest kit (Murex Biotech Limit, British). To this end, first, each blood sample (non-citrated) was mixed well with a soybean trypsin inhibitor and Bothrops atrox venom and incubated at 37° C. for 30 min. After centrifugation at 1,500×g for 10 min twice, the supernatant serum was diluted with a glycine saline buffer. 50 µl of the diluted serum was mixed with a drop of a latex suspension on a test slide glass and spread uniformly. The slide was placed in a shaker for 2 min and observed for agglutination. The concentration of FDP was determined semi-quantitatively as follows: with 1:0 dilution (−):0 µg/ml, (+):1 µg/ml, (++):2 µg/ml; with 1:1 dilution, (+):3 µg/ml, (++) :4 µg/ml; with 1:2 dilution (+):5 µg/ml, (++):6 µg/ml, etc.

For the assay of S-GOT, S-GPT and BUN, diagnostic kits (Boehringer Mannheim; AST kit for S-GOT, ALT kit for S-GPT, and urea kit for BUN) were used, together with an automatic biochemical analyzer (Hitachi 747), with the help of Green Cross Reference Lab., Korea.

When a septic shock was induced in test animals by injecting LPS over a long period of time, the indices of DIC and MOF were improved by the oral administration of the compounds of Chemical Formulas 1 and 2. In a control administered only with LPS, a sudden decrease of the platelet number and fibrinogen level in blood and an extension of the PT and aPTT were observed. Also, the FDP level in blood was remarkably increased. In addition, high S-GOT, S-GPT and BUN values were detected, indicating that the function of the liver or the kidney was degraded. An improvement was observed in the indices for these DIC and MOF syndromes when the compounds of Chemical Formulas 1 and 2 were orally administered.

In detail, after oral administration of higenamine or the compounds of Chemical Formulas 1 and 2, LPS (20 mg/kg) was injected into rats over a 3 hour period to cause DIC and MOF. In order to examine the improvement in the indices for DIC and MOF, these test animals were compared with a control which was provided with LPS only.

Figure 3:
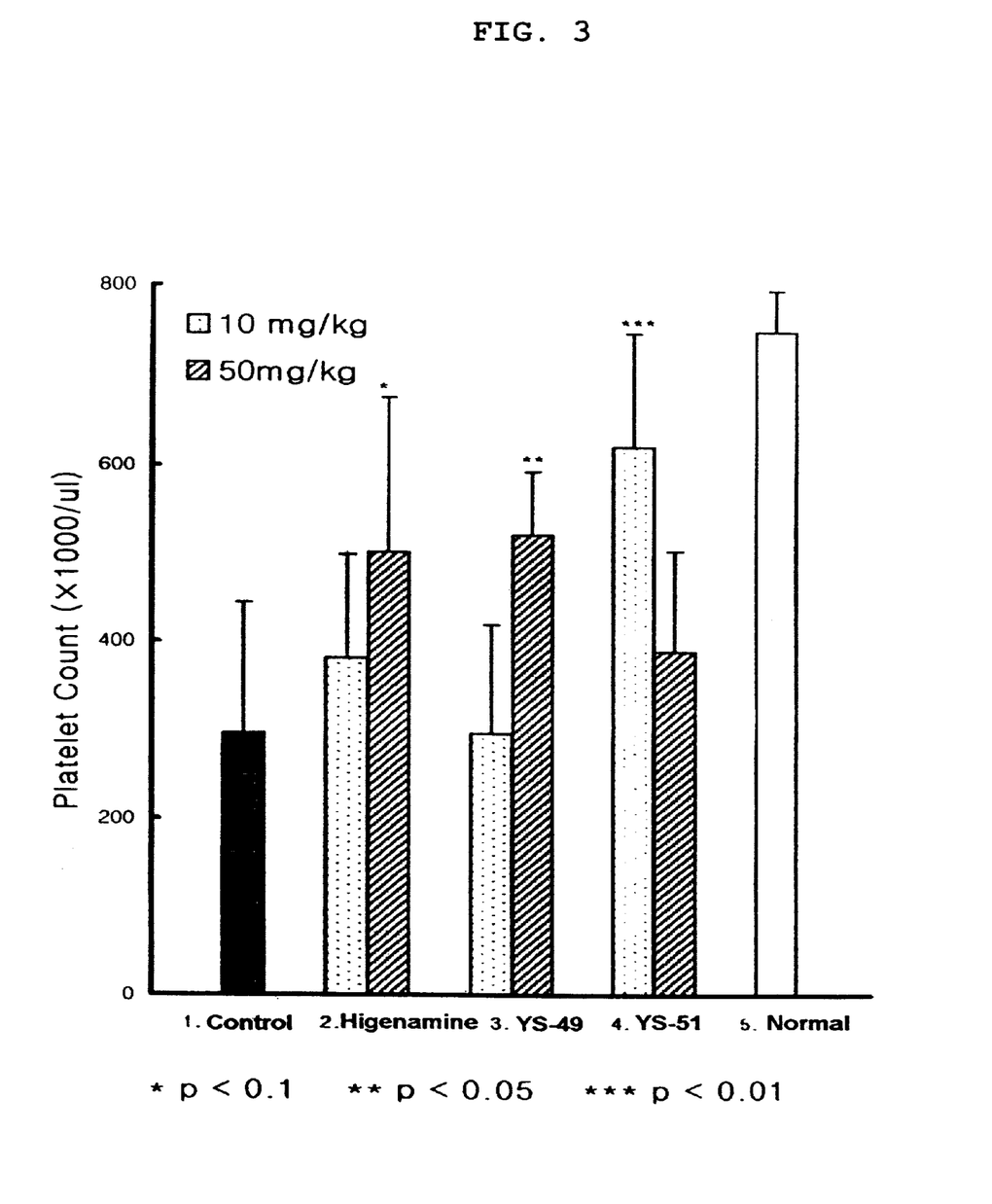
FIG. 3 is a graph showing changes of the platelet number in blood when LPS (20 mg/kg) is intravenously infused into rats over a 3 hour period after 1 hour from the last oral administration of higenamine and the compounds of Chemical Formulas 1 and 2.
Figure 4:
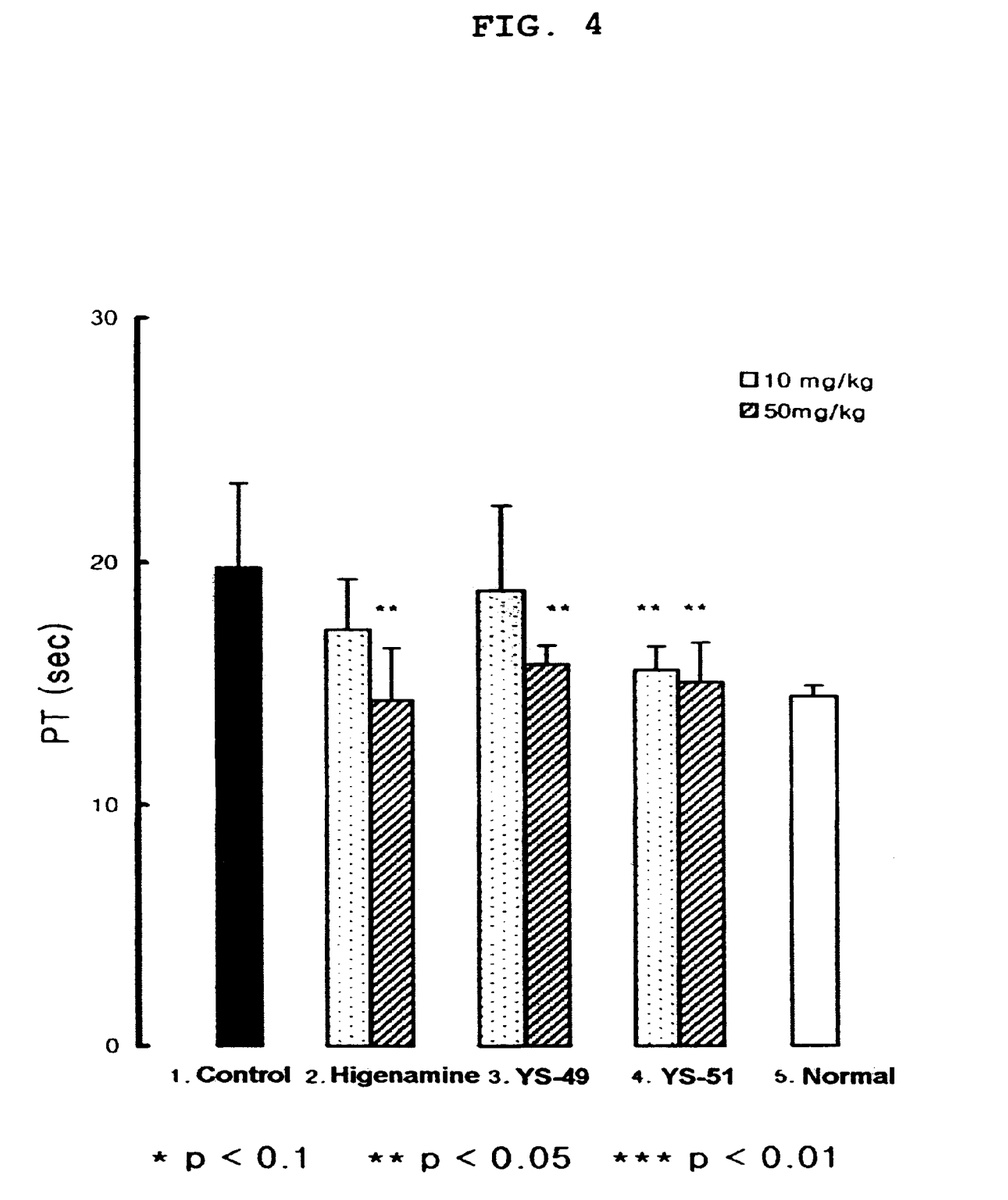
FIG. 4 is a graph showing changes of the prothrombin time when LPS (20 mg/kg) is intravenously infused to rats over a 3 hour period after 1 hour from the last oral administration of higenamine and the compounds of Chemical Formulas 1 and 2.
Figure 5:
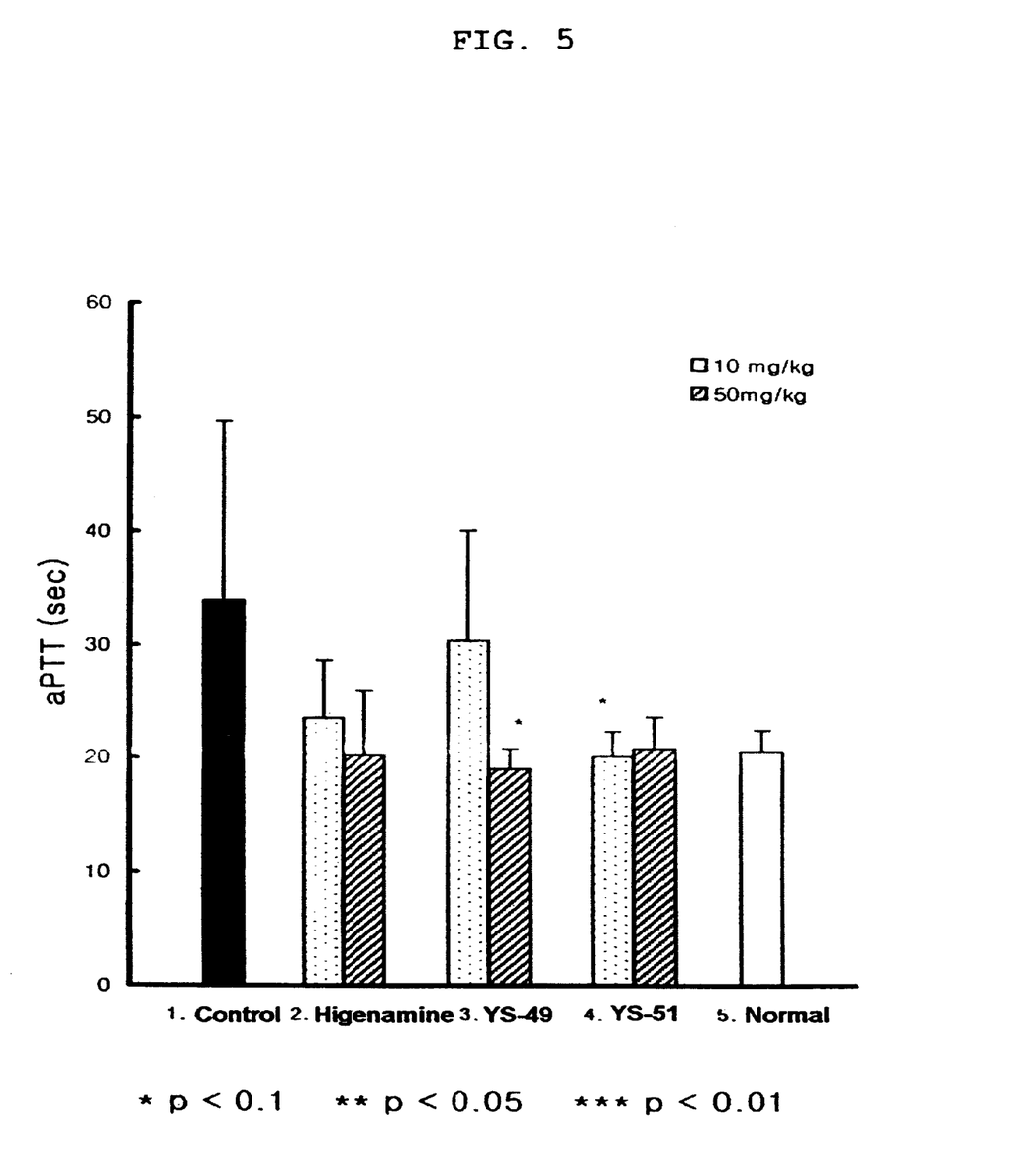
FIG. 5 is a graph showing changes of the activated partial thromboplastin time (aPTT) when LPS (20 mg/kg) is intravenously infused to rats over a 3 hour period after 1 hour from the last oral administration of higenamine and the compounds of Chemical Formulas 1 and 2.
Figure 6:
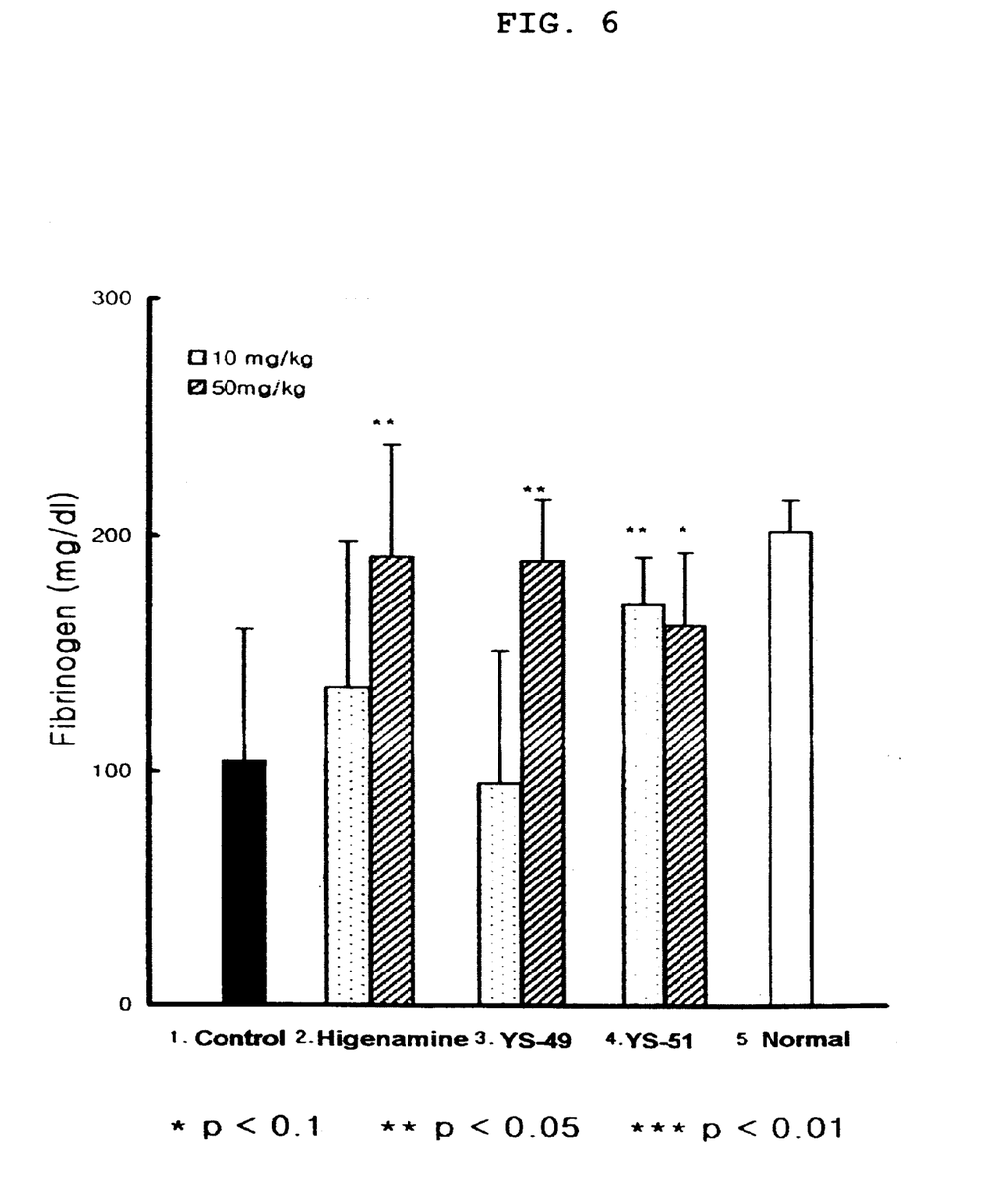
FIG. 6 is a graph showing changes of the fibrinogen level in blood when LPS (20 mg/kg) is intravenously infused to rats over a 3 hour period after 1 hour from the last oral administration of higenamine and the compounds of Chemical Formulas 1 and 2.
Figure 7:
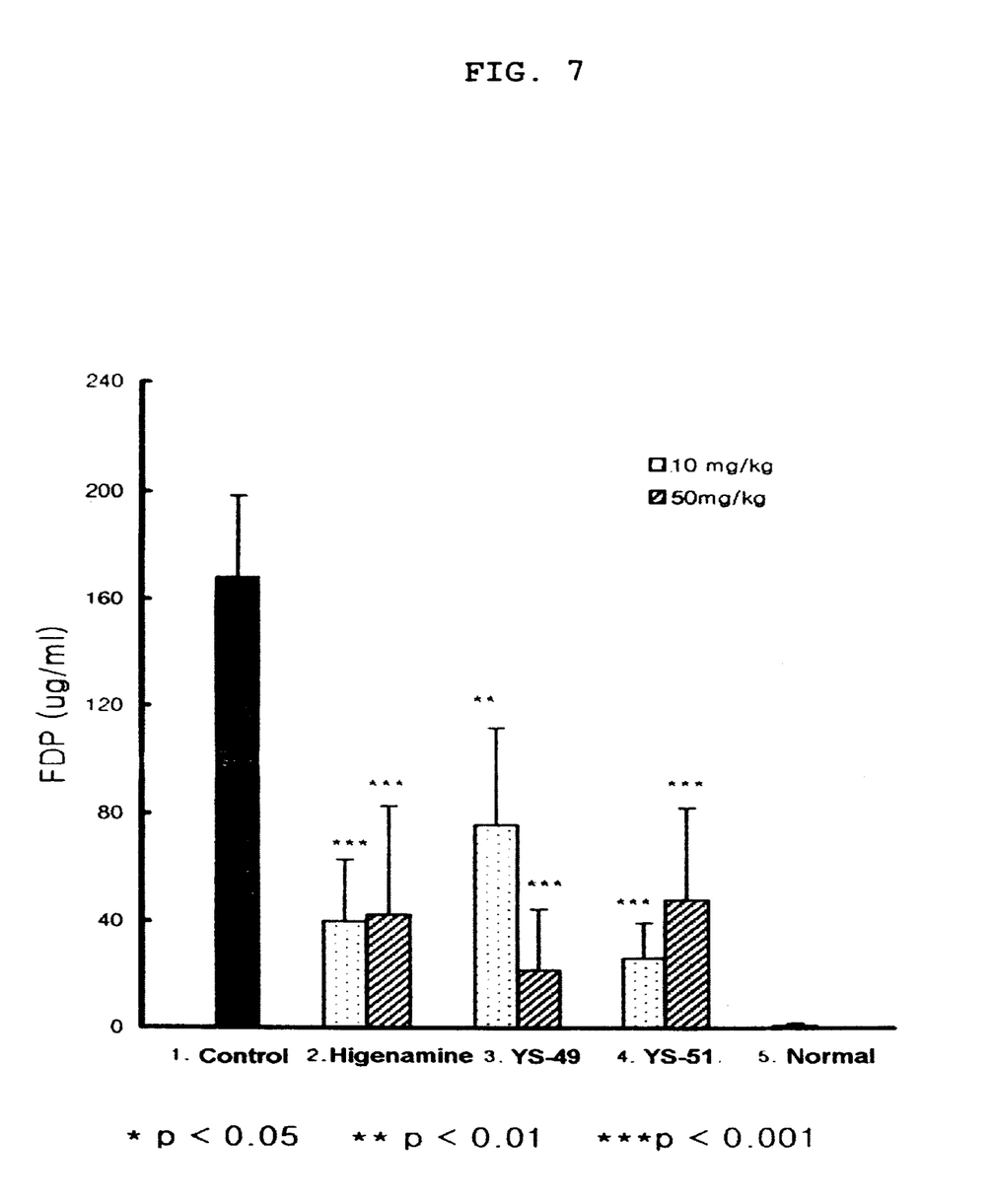
FIG. 7 is a graph showing changes of the fibrin/fibrinogen dehydrogenation product (FDP) level in blood when LPS (20 mg/kg) is intravenously infused to rats over a 3 hour period after 1 hour from the last oral administration of higenamine and the compounds of Chemical Formulas 1 and 2.

As for the control, it had $296 \times 10^3$ latelets per µl of blood, which is below half of the platelet number of the normal ($747 \times 10^3$/µl) as shown in FIG. 3. PT and aPTT were measured to be 19 and 33 sec, respectively, which were extended by 50% compared with those of the normal (14 and 20 sec) (see FIGS. 4 and 5). The control had a fibrinogen concentration of 104 mg/ml and an FDP concentration of 168 µg/ml while the normal maintained a fibribnogen level at 202 mg/ml and an FDP level at 1 µg/ml. As compared with the normal, the control was reduced to half in fibrinogen level and remarkably increased in FDP level, which indicated that DIC was seriously aggravated (see FIGS. 6 and 7). In addition, S-GOT, S-GPT and BUN levels were 231.0 U/l, 60.8 U/l and 25.6 mg/dl, respectively, which were higher than corresponding ones of the normal (167 U/l, 49.3 U/l and 15.0 mg/dl). That is, MOF was also seriously aggravated.

Figure 8:
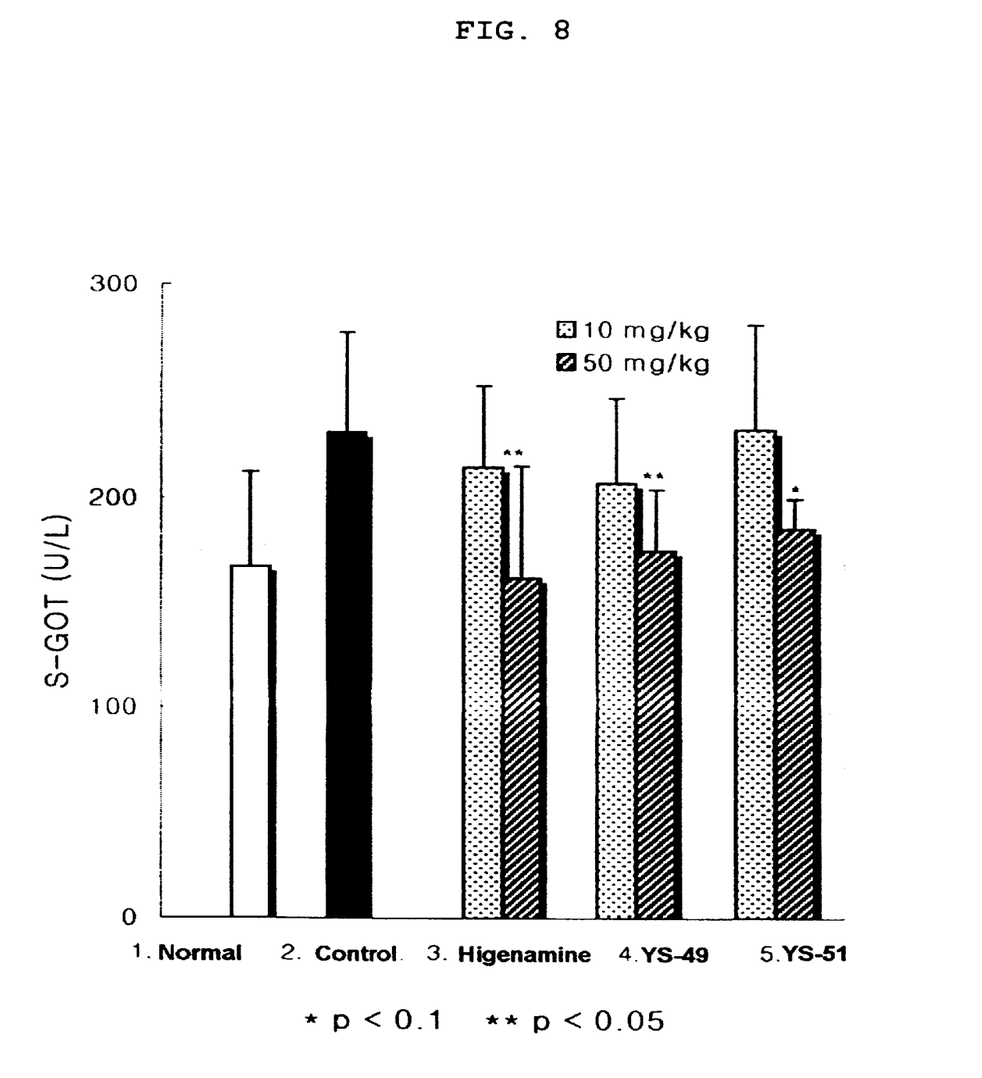
FIG. 8 is a graph showing changes of the S-GOT level in blood when LPS (20 mg/kg) is intravenously infused to rats over a 3 hour period after 1 hour from the last oral administration of higenamine and the compounds of Chemical Formulas 1 and 2.
Figure 9:
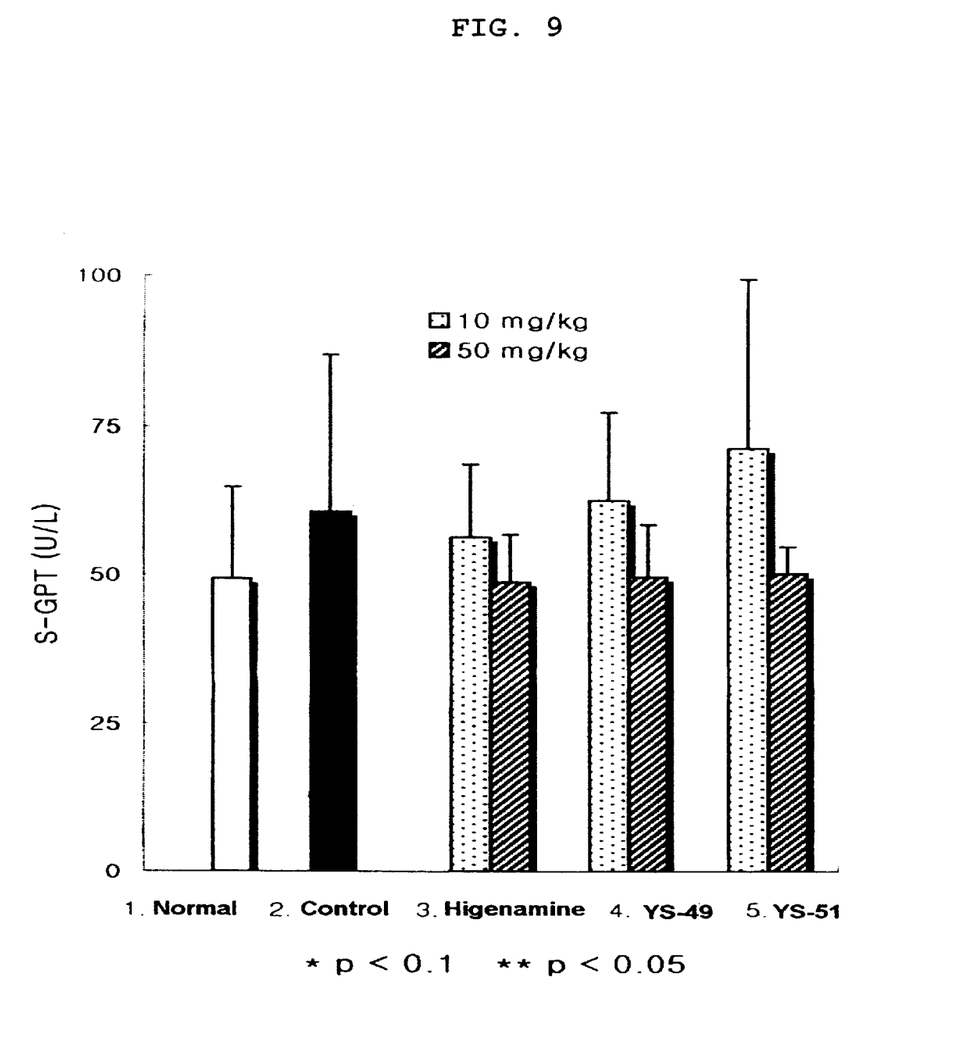
FIG. 9 is a graph showing changes of the S-GPT level in blood when LPS (20 mg/kg) is intravenously infused to rats over a 3 hour period after 1 hour from the last oral administration of higenamine and the compounds of Chemical Formulas 1 and 2.
Figure 10:
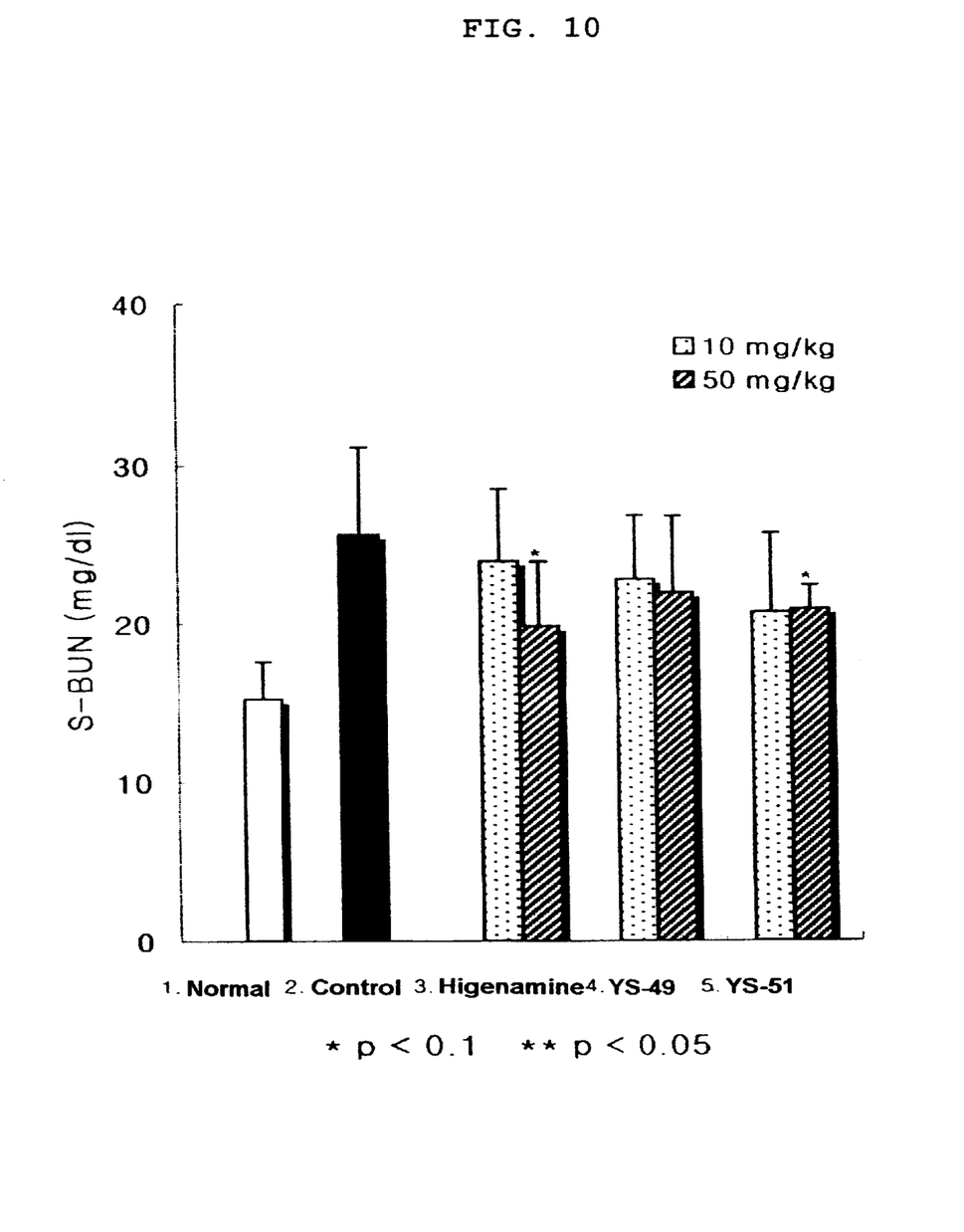
FIG. 10 is a graph showing changes of the BUN level in blood when LPS (20 mg/kg) is intravenously infused to rats over a 3 hour period after 1 hour from the last oral administration of higenamine and the compounds of Chemical Formulas 1 and 2.

However, oral administration of higenamine or the compound of Chemical Formulas 1 or 2 at both doses of 10 mg/kg and 50 mg/kg ameliorated the indices for DIC and MOF as compared with the control which was administered with LPS only. That is, the number of platelets was increased, the PT and aPTT were shortened, the fibrinogen level was increased, and the FDP level was decreased as shown in FIGS. 3 to 7. Also, a reduction was brought about in S-GOT, S-GPT and BUN levels as shown in FIGS. 8 to 10. From these results, it is apparent that the compounds of the present invention can improve LPS-induced DIC and MOF.

EXPERIMENTAL EXAMPLE IX

Preventive Effect on LPS-caused Death

When a large quantity of LPS is injected into animals, various diseases, such as DIC, are generated and they are dead of septic shock in a short period of time. In this experiment, LPS (20 mg/kg) was intraperitoneally injected into mice and the number of mice which were alive for 48 hours after the injection, was counted. Also, an examination was made of the influence of test drugs on the survival ratio.

LPS (20 mg/kg) was administered to mice by injection (i.p.), after which the mice alive were countered every 6 hours for 48 hours. 30 min before LPS injection, test drugs were intraperitoneally injected into the mice to examine the preventive effect on the LPS-caused death.

Figure 11A:
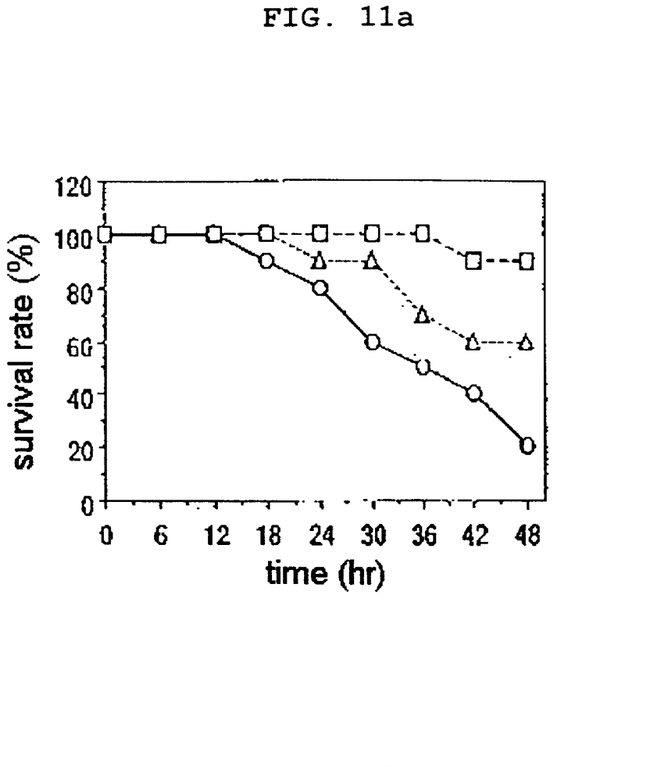
FIG. 11a is a graph showing the suppressive effect of the compound of Chemical Formula 1 on LPS-caused death in mice, in which -○-: LPS (20 mg/kg)
Figure 11B:
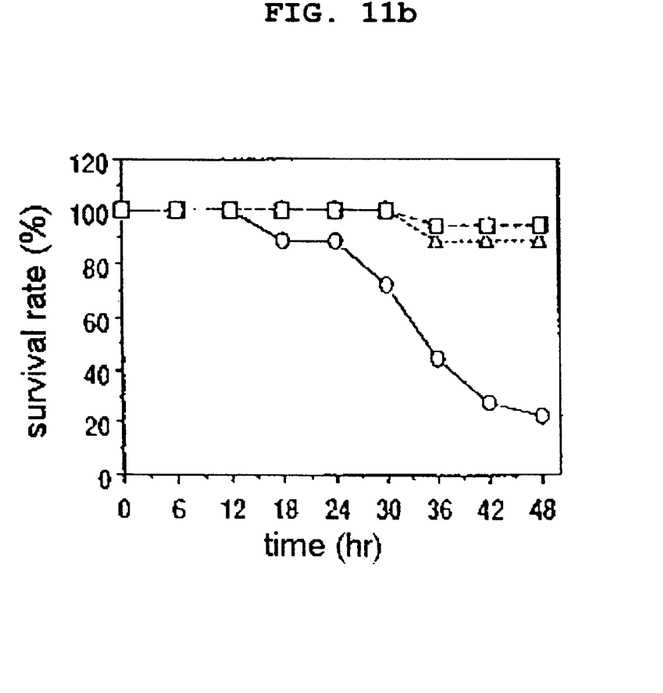
FIG. 11b is a graph showing the suppressive effect of the compound of Chemical Formula 2 on LPS-caused death in mice, in which -○-: LPS (20 mg/kg)

When injecting LPS only, the survival rate of mice after 48 hours was about 20%. However, upon pre-treatment with a dose of 20 mg/kg of the compound of Chemical Formula 1 (FIG. 11a) and the compound of Chemical Formula 2 (FIG. 11b) prior to the injection of LPS, no mice were dead until 30 hours after the LPS injection and 90% or more of the mice were alive even after 48 hours. When higenamine or the compound of Chemical Formula 2 was injected at a dose of 10 mg/kg, 80% of the mice survived up until 48 hours. When being injected at a dose of 10 mg/kg, the compound of Chemical Formula 1 showed a survival rate of 60% until 48 hours. Therefore, the compounds of Chemical Formulas 1 and 2 have protective activity against LPS-caused shock.

INDUSTRIAL APPLICABILITY

As described hereinbefore, each of the compounds of Chemical Formulas 1 and 2 shows inhibitory activity against platelet aggregation and iNOS expression as well as heart stimulating activity and hypotensive activity, in combination and at once, so they can be used as therapeutic agents for heart failure. These compounds can also be used as an antithrombotic agent by taking advantage of their inhibitory activity against platelet aggregation and as a tissue injury inhibitor, a septicemia curative or a therapeutic agent for DIC by virtue of their suppressive activity against iNOS expression and NO production. In addition, the pharmaceutical compositions containing the compounds of the present invention are wide in safety margin and show a long drug effect period of time.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for the therapeutic treatment of Septicemia, comprising administering a does of a pharmaceutical composition comprising 1-α-naphthylmethyl-6,7-dihydroxy-1,2,3,4-tetrahydroisoquinoline and/or 1-β-naphthylmethyl-6,7-dihydroxy-1,2,3,4-tetrahydroisoquinoline as a pharmacologically active ingredient.

2. The method as set forth in claim 1, wherein Septicemia is caused by the activation of blood coagulation, comprising rapid decrease in the number of platelets, bleeding, shock, thrombosis, and vascular infarction.

3. The method as set forth in claim 2, wherein Septicemia is caused by DIC and complex tissue injury.

4. The method as set forth in claim 2, wherein 1-α-naphthylmethyl-6,7-dihydroxy-1,2,3,4-tetrahydroisoquinoline shows inhibitory activity against platelet aggregation.

* * * * *